United States Patent [19]

Reifschneider

[11] Patent Number: 4,729,987
[45] Date of Patent: Mar. 8, 1988

[54] INSECTICIDAL O,O-DIETHYL-O-(2-(1,1-DIMETHYLETHYL)-5-PYRIMIDINYL)-PHOSPHOROTHIOATE

[75] Inventor: Walter Reifschneider, Walnut Creek, Calif.

[73] Assignee: The Dow Chemical Company, Midland, Mich.

[21] Appl. No.: 921,300

[22] Filed: Oct. 21, 1986

Related U.S. Application Data

[63] Continuation of Ser. No. 688,774, Jan. 4, 1985, abandoned, which is a continuation of Ser. No. 521,516, Aug. 9, 1983, abandoned, which is a continuation of Ser. No. 300,422, Sep. 9, 1981, abandoned, which is a continuation of Ser. No. 928,665, Jul. 28, 1978, Pat. No. 4,429,125.

[51] Int. Cl.$^4$ .................. A01N 57/16; C07F 9/65
[52] U.S. Cl. ....................... 514/86; 544/243
[58] Field of Search ................ 544/243; 514/86

[56] References Cited

U.S. PATENT DOCUMENTS

| | | | |
|---|---|---|---|
| 2,754,243 | 7/1956 | Gysin et al. | 424/200 |
| 3,907,797 | 9/1975 | Budesinsky et al. | 544/298 |
| 4,093,718 | 6/1978 | Maurer et al. | 424/200 |
| 4,127,652 | 11/1978 | Maurer et al. | 424/200 |
| 4,150,159 | 4/1979 | Maurer et al. | 424/200 |
| 4,152,427 | 5/1979 | Maurer et al. | 424/200 |
| 4,325,948 | 4/1982 | Maurer et al. | 424/200 |
| 4,429,125 | 1/1984 | Reifschneider | 544/243 |
| 4,444,764 | 4/1984 | Reifschneider et al. | 424/200 |
| 4,474,958 | 10/1984 | Reifschneider | 544/334 |
| 4,486,422 | 12/1984 | Costales et al. | 544/243 X |
| 4,558,039 | 12/1985 | Reifschneider et al. | 514/86 |
| 4,654,329 | 3/1987 | Reifschneider | 514/86 |
| 4,666,894 | 5/1987 | Maurer et al. | 514/86 |

FOREIGN PATENT DOCUMENTS

| | | |
|---|---|---|
| 0858996 | 3/1978 | Belgium . |
| 0003098 | 7/1979 | European Pat. Off. . |
| 0004644 | 10/1979 | European Pat. Off. . |
| 2747357 | 4/1979 | Fed. Rep. of Germany . |
| 2801584 | 7/1979 | Fed. Rep. of Germany . |
| 1540968 | 2/1979 | United Kingdom . |

OTHER PUBLICATIONS

Budesinsky, Ceskoslov, farm., 10, pp. 241–247 (1961).
Hurst, et al., J. Chem. Soc., 1965, pp. 7116–7119 (1965).
Budesinsky, et al., Coll. Czech. Chem. Commun., 40, pp. 1078–1088 (1975).
Feutrill, et al., Austrailian J. Chem., 25, pp. 1719–1729 (1972).

Primary Examiner—Donald G. Daus
Assistant Examiner—Diana G. Rivers
Attorney, Agent, or Firm—Edward E. Schilling; Ronald G. Brookens

[57] ABSTRACT

Compounds of the formula:

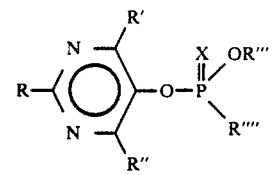

wherein
R is hydrogen; alkyl of 1 to 8 carbons; alkylthiomethyl, alkylsulfinylmethyl or alkylsulfonylmethyl wherein alkyl contains 1 to 4 carbons; phenyl; phenylthio; alkylthio, alkylsulfinyl or alkylsulfonyl wherein alkyl contains 1 to 4 carbons; or alkylthioethylthio wherein alkyl contains 1 to 2 carbons;
R' is hydrogen, methyl or alkylthio of 1 to 2 carbons;
R" is hydrogen or methyl;
X is oxygen or sulfur;
R'" is alkyl of 1 to 2 carbons; and
R"" is —OR'" or —S-alkyl of 1 to 4 carbons, are highly useful insecticides which are particularly valuable when applied to the soil, but are also useful applied to foliage of crops or trees. Especially good control is obtained of corn rootworm, codling moth, thrips, leafhoppers, and nematodes. The compounds are conveniently applied in the form of a composition containing a pesticidal carrier such as an inert solvent or a finely divided inert solid in which case the composition is preferably granulated. An effective application rate is in the range of about 0.1 to about 5 pounds per acre when soil incorporated, and about 0.5 to about 2,000 ppm for foliar applications.

6 Claims, No Drawings

INSECTICIDAL O,O-DIETHYL-O-(2-(1,1-DIMETHYLETHYL)-5-PYRIMIDINYL)-PHOSPHOROTHIOATE

CROSS REFERENCE TO RELATED APPLICATIONS

This is a continuation of application Ser. No. 688,744, filed Jan. 4, 1985, now abandoned: in turn a continuation of application Ser. No. 521,516, filed Aug. 9, 1983, now abandoned; in turn a continuation of application Ser. No. 300,422, filed Sept. 9, 1981, now abandoned; and in turn a continuation of application Ser. No. 928,665, filed July 28, 1978, now U.S. Pat. No. 4,429,125.

BACKGROUND OF THE INVENTION

1. Field of the Invention

The invention relates to highly useful pyrimidinyl phosphates, phosphorothioates and phosphorodithioates which are effective insecticides particularly against corn rootworm, thrips, leafhoppers and nematodes when applied to the soil of such crops as corn, sorghum, cotton and sugar beets, and codling moth, best army worm, tobacco budworm, bollworm and cabbage looper when applied to the foliage of appropriate crops.

2. Description of Prior Art

It has long been a desired objective in the art to provide an insecticide effective and useful in the control of soil pests or insects such as corn rootworm. It is also desirable to provide an insecticide with systemic activity whereby the insecticide can be soil incorporated and to have the insecticide taken up effectively by growing crops and delivered to the point of attack by insects by systemic activity or translocation within the plant. It is, moreover, desirable to provide an effective, useful insecticide for the control of chewing, sucking insects upon making foliar application of the pesticide on the plants to be protected.

Phosphate esters similar to the present compounds are described in U.S. Pat. No. 2,754,423, which discloses the compound 0,0-diethyl 0-(2-(1-methylethyl)-4-methyl-6-pyrimidinyl) phosphorothioate which is sold commercially under the mark DIAZINON. The patented compounds are made from 6-pyrimidinols whereas the present compounds are prepared from 5-pyrimidinols. The present compounds have surprisingly greater activity and effectiveness than do the corresponding patented compounds with similar ring substituents, particularly against a rather broad spectrum of insects combated by application of the active ingredient to the soil of a crop such as corn, sorghum, cotton, potatoes and sugar beets, as well as against insects controlled by foliar application of the pesticide.

Other pyrimidinyl phosphate esters prepared from 2-pyrimidinols or 4-pyrimidinols are well known to the art.

Some of the present compounds and their insecticidal use are described in Belgian Patent No. 858,996 published Mar. 23, 1978.

SUMMARY OF THE INVENTION

The novel, highly useful compounds of the invention are those of the following formula:

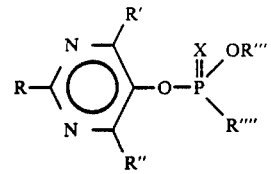

wherein
R is hydrogen; alkyl of 1 to 8 carbons; alkylthiomethyl, alkylsulfinylmethyl or alkylsulfonylmethyl wherein alkyl contains 1 to 4 carbons; phenyl; phenylthio; alkylthio; alkylsulfinyl or alkylsulfonyl wherein alkyl contains 1 to 4 carbons; or alkylthioethylthio wherein alkyl contains 1 to 2 carbons;
R' is hydrogen, methyl or alkylthio of 1 to 2 carbons;
R'' is hydrogen or methyl;
X is oxygen or sulfur;
R''' is alkyl of 1 to 2 carbons; and
R'''' is —OR''' or —S—alkyl of 1 to 4 carbons.

These compounds are highly useful in the control of troublesome insects, particularly corn rootworm, thrips, leafhoppers and nematodes when applied to the soil. Compositions containing from about 0.05 to about 20% by weight are useful for soil application or to other substrates as in foliar applications to control chewing and sucking insects. Useful concentrates contain from about 5 to about 98% by weight active ingredient. Soil application rates are primarily in the range of about 0.1 to about 2 pounds of active ingredient per acre. Foliar applications are made of compositions containing from about 0.5 to about 2,000 ppm of active ingredient.

MORE DETAILED DESCRIPTION OF THE INVENTION

The present compounds are largely somewhat viscous oils, or, solids melting below about 100° C., which are rather readily soluble in many common organic solvents such as xylene or acetone or petroleum distillates and of very low solubility in water. The compounds are useful as pesticides and are especially adapted to be employed as active toxicants in compisitions for the control of a number of insects such as corn rootworm, western spotted cucumber beetle, leafhopper, codling moth, tobacco budworm, beet armyworm, thrips, cabbage looper, black cutworm, German roach, cotton leaf worm, pink bollworm, spiny bollworm, rice stem borer, aphids, wire worm, root knot nematode and sugar beet nematode.

The novel compounds of the present invention are prepared from the appropriate 5-pyrimidinols of the following general formula:

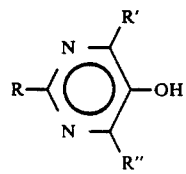

wherein
R is hydrogen; alkyl of 1 to 8 carbons; alkylthiomethyl, alkylsulfinylmethyl or alkylsulfonylmethyl wherein alkyl contains 1 to 4 carbons; phenyl; phenylthio, alkylthio, alkylsulfinyl or alkylsulfonyl wherein alkyl contains 1 to 4 carbons; or alkylthioethylthio wherein alkyl contains 1 to 2 carbons;

R' is hydrogen, methyl or alkylthio of 1 to 2 carbons; and

R" is hydrogen or methyl;

upon reaction with the appropriate phosphorochloridate or phosphorochloridothioate or phosphorochloridodithioate of the following general formula:

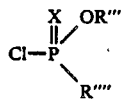

wherein

X is oxygen or sulfur;

R''' is alkyl of 1 to 2 carbons; and

R'''' is —OR''' or —S alkyl of 1 to 4 carbons.

It is to be understood that throughout the specification and claims that "alkyl" refers to both straight chained and branched alkyl.

The reaction is carried out conveniently in an inert organic liquid such as benzene, toluene, xylene, chlorobenzene, petroleum ether, methylene chloride, chloroform, carbon tetrachloride, ethers, such as diethyl ether, dibutyl ether and dioxane, ketones, such as acetone, methyl ethyl ketone, methyl isopropyl ketone or methyl isobutyl ketone, and nitriles, such as acetonitrile and propionitrile.

Also employed is an acid binding agent or acceptor selected from alkali carbonates, alkali hydroxides, and alcoholates such as sodium carbonate, potassium carbonate, sodium or potassium methylate or ethylate and aliphatic, aromatic or heterocyclic amines, for example, triethylamine, trimethylamine, dimethylaniline, dimethylbenzylamine and pyridine.

The reaction temperature can be selected from a rather large range between about 0 to about 100° C., preferably about 20 to about 60° C. The reaction is generally carried out under ambient atmospheric pressure conditions.

The amounts of the reagents to be employed are not critical, some of the desired products being obtained when employing any proportion of the reactants. In the preferred method of operation, good results are obtained when employing substantially equimolecular proportions of the pyrimidinol and phosphorochloridate or phosphorochloridothioate. The reaction takes place smoothly at the temperature range from 0° to 100° C. with the production of the desired product and chloride by-product. In carrying out the reaction, the reactants are mixed and contacted together in any convenient fashion, and the resulting mixture maintained for a period of time in the reaction temperature range to complete the reaction. Following the completion of the reaction, the reaction mixture is washed with water and any organic reaction medium removed by distillation under reduced pressure to obtain the desired product as a residue. This product can be further purified by conventional procedures such as washing with water and dilute aqueous alkali metal hydroxide, solvent extraction and recrystallization.

The phosphorochloridates or phosphorochloridothioates which are employed as intermediates are prepared according to methods well known in the art. In the case of the dithioates, the intermediate may be prepared in several steps by reacting PCl₃ with the appropriate alkylsulfenylchloride in the presence of sulfur dioxide to obtain S-alkyl phosphorodichloridothioate which is then reacted with phosphorous pentasulfide to obtain S-alkyl phosphorodichloridodithioate. This latter compound is then reacted with ethanol in the presence of an acid acceptor such as triethylamine, producing however a mixture of the desired product, O-ethyl S-alkyl phosphorochloridodithioate, starting material and a by-product, O,O-diethyl S-alkyl phosphorodithioate, which mixture must be resolved. More preferably the ammonium salt of O,O-diethyl dithiophosphoric acid is alkylated with the appropriate alkyl bromide to give the S-alkyl O,O-diethyl phosphorodithioate which is then treated with sodium hydrogen sulfide or with sodium ethylmercaptide to give the sodium salt on cleaving of one of the ethyl groups. The sodium salt is then reacted with phosphorous pentachloride to yield the desired O-ethyl S-alkyl phosphorochloridodithioate.

The following examples merely illustrate the invention and are not to be construed as limiting:

EXAMPLE 1

O,O-diethyl O-(2-(1,1-dimethylethyl)-5-pyrimidinyl) phosphorothioate

To a mixture of 98 grams of 2-(1,1-dimethylethyl)-5-pyrimidinol, 130 grams of finely powdered potassium carbonate and 800 ml of acetonitrile was added 121 grams of O,O-diethyl phosphorochloridothioate. The temperature of the reaction mixture rose to 55° C. Stirring was continued until no more starting O,O-diethyl phosphorochloridothioate could be detected by gas-liquid chromatography. The reaction appeared to be complete in about 1 hour. The salts present were then removed by filtration, the filtrate concentrated in a rotary evaporator, the residue taken up in ether, the ether solution washed twice with 2 percent aqueous sodium hydroxide, and once with saturated sodium chloride solution, and dried over anhydrous sodium sulfate. The ether was then removed under vacuum leaving a pale yellow colored oil with a refractive index at 25° of 1.4913. On elemental analysis the product was found to contain by weight 47.38% carbon; 6.67% hydrogen and 9.19% nitrogen. Theoretical analysis is 47.35% carbon; 6.96% hydrogen and 9.21% nitrogen.

EXAMPLE 2

O,O-diethyl O-(2-(1-methylethyl)-5-pyrimidinyl) phosphorothioate

To a stirred mixture of 166 grams of 2-(1-methylethyl) 5 pyrimidinol, 230 grams of finely powdered potassium carbonate and 1400 ml of acetonitrile was added in a slow stream 226 grams of O,O-diethyl phosphorochloridothioate. The mixture warmed to 55°. Stirring was continued until no more O,O-diethyl phosphorochloridothioate could be detected by GLC. The solids present were removed by filtration, the filtrate concentrated under vacuum, the residue taken up in diethyl ether, the ether solution washed twice with 2% aqueous sodium hydroxide, and once with saturated sodium chloride solution and dried over anhydrous sodium sulfate. The ether was removed under vacuum leaving a pale yellow oil having a refractive index at 25° of 1.4944. On elemental analysis the product was found to contain 45.68% carbon; 6.54% hydrogen and 9.57% nitrogen. Theoretical is 45.50% carbon; 6.60% hydrogen and 9.65% nitrogen.

EXAMPLE 3

O,O-dimethyl O-(2-(1,1-dimethylethyl)-5-pyrimidinyl) phosphorothioate

To a stirred mixture of 6 grams of 2-(1,1-dimethylethyl)-5-pyrimidinol, 6 grams of finely powdered potassium carbonate and 40 ml of acetonitrile was added 6.33 grams of O,O-dimethyl phosphorochloridothioate. The mixture was stirred without external heating until all O,O-dimethyl phosphorochloridothioate was consumed as shown by GLC. The solids present were removed by filtration, the filtrate concentrated under vacuum, the residue taken up in diethyl ether, the ether solution washed twice with 2% aqueous sodium hydroxide, once with saturated sodium chloride solution and dried over anhydrous sodium sulfate. The solvent was removed under vacuum, while leaving a pale amber colored oil having a refractive index at 25° of 1.5027. Elemental analysis showed the product to contain 43.82% carbon; 6.09% hydrogen and 10.10% nitrogen. Theoretical composition is 43.47% carbon; 6.20% hydrogen and 10.14% nitrogen.

EXAMPLE 4

O (2- ethyl-5-pyrimidinyl) S-(2-methylpropyl) phosphorodithioate

A mixture of 5 grams of 2-ethyl-5-pyrimidinol, 5 grams of finely powdered potassium carbonate, 40 ml of acetonitrile and 9.3 grams of O-ethyl S-(2-methylpropyl) phosphorochloridodithioate was stirred without external heating overnight. The solids were then removed by filtration, the filtrate concentrated under vacuum, the residue taken up in diethyl ether, the ether solution washed twice with 2% aqueous sodium hydroxide, once with saturated sodium chloride solution and dried over anhydrous sodium sulfate. The solvent was removed in a rotary evaporator leaving a pale amber colored oil having a refractive index of 25° of 1.5296. Elemental analysis showed the product contained 44.81% carion; 6.58% hydrogen and 8.59% nitrogen. Theoretical analysis is 44.98% carbon; 6.61% hydrogen aid 8.74% nitrogen.

EXAMPLE 5

O,O-dimethyl O-(2-((1-methylethyl)thio)-5-pyrimidinyl) phosphorothioate

A mixture of 4 grams of 2-((1-meth-ylethyl)thio)5-pyrimidinol, 4 grams of finely powdered potassium carbonate, 40 ml of acetonitrile and 4 grams of O,O-dimethyl phosphorochloridothioate was stirred and heated to 45° until no more O,O-dimethyl phosphorochloridothioate could be detected by GLC. The solids were then removed by filtration and the filtrate concentrated under vacuum. The residual oil was taken up in ether, the ether solution washed once with 2% aqueous sodium hydroxide, once with saturated sodium chloride solution and dried over anhydrous sodium sulfate. The ether was removed by distillation leaving a pale amber colored oil which crystallized on standing. The material was recrystallized from hexane to give 6.4 grams of white crystals melting at 44-46°. On elemental analysis the product was found to contain 36.70% carbon; 5.06% hydrogen and 9.43% nitrogen. Theoretical analysis is 36.72% carbon; 5.14% hydrogen and 9.52% nitrogen.

| Compound | Index of Refraction at 25° or melting Temperature °C. |
| --- | --- |
| O,O—diethyl O—(5-pyrimidinyl) phosphorothioate | 1.5041 |
| O,O—diethyl O—(2-methyl-5-pyrimidinyl) phosphorothioate | 1.5017 |
| O,O—diethyl O—(2-ethyl-5-pyrimidinyl) phosphorothioate | 1.4992 |
| O,O—diethyl O—(2-(n-propyl)-5-pyrimidinyl) phosphorothioate | 1.4947 |
| O,O—dimethyl O—(2-(n-butyl)-5-pyrimidinyl) phosphorothioate | 1.4929 |
| O,O—diethyl O—(2-(2-methyl propyl)-5-pyrimidinyl) phosphorothioate | 1.4936 |
| O,O—diethyl O—(2-pentyl-5-pyrimidinyl) phosphorothioate | 1.4913 |
| O,O—diethyl O—(2-octyl-5-pyrimidinyl) phosphorothioate | 1.4890 |
| O,O—diethyl O—(2-phenyl-5-pyrimidinyl) phosphorothioate | 1.5698 |
| O,O—diethyl O—(2-(methylthio)methyl-5-pyrimidinyl) phosphorothioate | 1.5325 |
| O,O—diethyl O—(2-(methylsulfinyl)methyl-5-pyrimidinyl) phosphorothioate | 1.5412 |
| O,O—diethyl O—(2-(ethylthio)methyl-5-pyrimidinyl) phosphorothioate | 1.5285 |
| O,O—diethyl O—(2-(ethylsulfinyl)methyl-5-pyrimidinyl) phosphorothioate | 1.5367 |
| O,O—diethyl O—(2-(ethylsulfonyl)methyl-5-pyrimidinyl) phosphorothioate | 1.5247 |
| O,O—diethyl O—(2-ethyl-4-methyl-5-pyrimidinyl) phosphorothioate | 1.4988 |
| O,O—diethyl O—(2-(1-methylethyl)-4-methyl-5-pyrimidinyl) phosphorothioate | 1.4952 |
| O,O—diethyl O—(4,6-dimethyl-5-pyrimidinyl) phosphorothioate | (oil) |
| O,O—diethyl O—(2,4,6-trimethyl-5-pyrimidinyl) phosphorothioate | (oil) |
| O,O—dimethyl O—(2-methyl-5-pyrimidinyl) phosphorothioate | 1.5155 |
| O,O—dimethyl O—(2-ethyl-5-pyrimidinyl) phosphorothioate | 1.5124 |
| O,O—dimethyl O—(2-(n-propyl)-5-pyrimidinyl) phosphorothioate | 1.5072 |
| O,O—dimethyl O—(2-(1-methylethyl)-5-pyrimidinyl) phosphorothioate | 1.5062 |
| O,O—dimethyl O—(2-(n-butyl)-5-pyrimidinyl) phosphorothioate | 1.5044 |
| O,O— dimethyl O—(2-(n-pentyl)-5-pyrimidinyl) phosphorothioate | 1.5005 |
| O,O—dimethyl O—(2-phenyl-5-pyrimidinyl) phosphorothioate | 69–71 |
| O,O—diethyl O—(2-(1-methylethyl)-5-pyrimidinyl) phosphate | 1.4672 |
| O,O—diethyl O—(2-phenyl-5-pyrimidinyl) phosphate | 1.5447 |
| O—ethyl S—propyl O—(5-pyrimidinyl) phosphorodithioate | 1.5485 |
| O—ethyl S—propyl O—(2-methyl-5-pyrimidinyl) phosphorodithioate | 1.5386 |
| O—ethyl S—propyl O—(2-ethyl-5-pyrimidinyl) phosphorodithioate | 1.5350 |
| O—ethyl S—propyl O—(2-(n-propyl)-5-pyrimidinyl) phosphorodithioate | 1.5312 |
| O—ethyl S—propyl O—(2-(1-methylethyl)-5-pyrimidinyl) phosphorodithioate | 1.5319 |
| O—ethyl S—propyl O—(2-(1,1-dimethylethyl)-5-pyrimidinyl) phosphorodithioate | 1.5240 |
| O—ethyl S—propyl O—(2-(methylthio)-methyl-5-pyrimidinyl) phosphorodithioate | 1.5657 |
| O—ethyl S—propyl O—(2-(methylsulfinylmethyl)-5-pyrimidinyl) phosphorodithioate | 1.5738 |
| O—ethyl S—propyl O—(2-(ethylthio)-methyl-5-pyrimidinyl) phosphorodithioate | 1.5610 |
| O—ethyl S—propyl O—(2-(ethylsulfinyl)-methyl-5-pyrimidinyl) phosphorodithioate | 1.5674 |

| Compound | Index of Refraction at 25° or melting Temperature °C. |
|---|---|
| O—ethyl S—propyl O—(2-(1-methylethyl)-4-methyl-5-pyrimidinyl) phosphorodithioate | 1.5270 |
| O—ethyl S—propyl O—(2-methylthio-5-pyrimidinyl) phosphorodithioate | 1.5788 |
| O—ethyl S—propyl O—(2-((1-methylethyl)thio)-5-pyrimidinyl) phosphorodithioate | 1.5645 |
| O—ethyl S—propyl O—(2-((1,1-dimethylethyl)thio)-5-pyrimidinyl) phosphorodithioate | 1.5597 |
| O,O—diethyl O—(2-methylthio-5-pyrimidinyl) phosphorothioate | 1.5440 |
| O,O—diethyl O—(2-methylsulfinyl-5-pyrimidinyl) phosphorothioate | (oil) |
| O,O—diethyl O—(2-methylsulfonyl-5-pyrimidinyl) phosphorothioate | (oil) |
| O,O—diethyl O—(2-ethylthio-5-pyrimidinyl) phosphorothioate | 1.5393 |
| O,O—diethyl O—(2-ethylsulfinyl-5-pyrimidinyl) phosphorothioate | 1.5369 |
| O,O—diethyl O—(2-ethylsulfonyl-5-pyrimidinyl) phosphorothioate | 1.5240 |
| O,O—diethyl O—(2-((1-methylethyl)thio)-5-pyrimidinyl) phosphorothioate | 1.5312 |
| O,O—diethyl O—(2-(1-methylethylsulfinyl)-5-pyrimidinyl) phosphorothioate | 1.5288 |
| O,O—diethyl O—(2-(1-methylethylsulfonyl)-5-pyrimidinyl) phosphorothioate | 1.5200 |
| O,O—diethyl O—(2-(n-butyl)thio-5-pyrimidinyl) phosphorothioate | 1.5308 |
| O,O—diethyl O—(2-(n-butyl)sulfinyl-5-pyrimidinyl) phosphorothioate | 1.5264 |
| O,O—diethyl O—(2-((1,1-dimethylethyl)thio)-5-pyrimidinyl) phosphorothioate | 1.5285 |
| O,O—diethyl O—(2-alkylthio-5-pyrimidinyl) phosphorothioate wherein alkyl equals ⅓CH₂CH═CH₂ and ⅔CH═CH—CH₃ | 1.5499 |
| O,O—diethyl O—(2-((methylthio)ethylthio)-5-pyrimidinyl) phosphorothioate | 1.5599 |
| O,O—diethyl O—(2-phenylthio-5-pyrimidinyl) phosphorothioate | 1.5790 |
| O,O—diethyl O—(2-methylthio-4-methyl-5-pyrimidinyl) phosphorothioate | 1.5397 |
| O,O—diethyl O—(2-methylsulfinyl-4-methyl-5-pyrimidinyl) phosphorothioate | 1.5376 |
| O,O—diethyl O—(2-methylsulfonyl-4-methyl-5-pyrimidinyl) phosphorothioate | 1.5247 |
| O,O—diethyl O—(2-ethylthio-4-methyl-5-pyrimidinyl) phosphorothioate | 1.5353 |
| O,O—diethyl O—(2-((1-methylethyl)thio)-4-methyl-5-pyrimidinyl) phosphorothioate | 1.5292 |
| O,O—diethyl O—(2-((1-methylethyl)sulfinyl-4-methyl-5-pyrimidinyl) phosphorothioate | 1.5295 |
| O,O—diethyl O—(2,4-bis(methylthio)-5-pyrimidinyl) phosphorothioate | 1.5768 |
| O,O—diethyl O—(2-methyl-4-ethylthio-5-pyrimidinyl) phosphorothioate | 1.5338 |
| O,O—dimethyl O—(2-methylthio-5-pyrimidinyl) phosphorothioate | 1.5639 |
| O,O—dimethyl O—(2-methylsulfonyl-5-pyrimidinyl) phosphorothioate | 87–89 |
| O,O—dimethyl O—(2-ethylthio-5-pyrimidinyl) phosphorothioate | 1.5563 |
| O,O—dimethyl O—(2-ethylsulfinyl-5-pyrimidinyl) phosphorothioate | 90–92 |
| O,O—dimethyl O—(2-ethylsulfonyl-5-pyrimidinyl) phosphorothioate | 1.5372 |
| O,O—dimethyl O—(2-((1-methylethyl)thio)-5-pyrimidinyl) phosphorothioate | 44–46 |
| O,O—dimethyl O—(2-((1-methylethyl)sulfinyl)-5-pyrimidinyl) phosphorothioate | 66–68 |
| O,O—dimethyl O—(2-((1-methylethyl)sulfonyl)-5-pyrimidinyl) phosphorothioate | 91–93 |
| O,O—dimethyl O—(2-(n-butylthio)-5-pyrimidinyl) phosphorothioate | 1.5435 |
| O,O—dimethyl O—(2-((1,1-dimethylethyl)thio)-5-pyrimidinyl) phosphorothioate | |
| O,O—dimethyl O—(2-alkylthio-5-pyrimidinyl) phosphorothioate wherein alkyl is ⅓CH₂CH═CH₂ and ⅔CH═CHCH₃ | 1.5672 |
| O,O—dimethyl O—(2-((methylthio)ethylthio)-5-pyrimidinyl) phosphorothioate | 1.5784 |
| O,O—dimethyl O—(2-methylthio-4-methyl-5-pyrimidinyl) phosphorothioate | 1.5567 |
| O,O—dimethyl O—(2-methylsulfinyl-4-methyl-5-pyrimidinyl) phosphorothioate | 1.5557 |
| O,O—dimethyl O—(2-methylsulfonyl-4-methyl-5-pyrimidinyl) phosphorothioate | 1.5381 |
| O,O—dimethyl O—(2-ethylthio-4-methyl-5-pyrimidinyl) phosphorothioate | 1.5488 |
| O,O—dimethyl O—(2-((1-methylethyl)thio)-4-methyl-5-pyrimidinyl) phosphorothioate | 1.5428 |
| O,O—dimethyl O—(2-((1-methylethyl)sulfinyl)-4-methyl-5-pyrimidinyl) phosphorothioate | 1.5454 |
| O,O—dimethyl O—(2-methyl-4-ethylthio-5-pyrimidinyl) phosphorothioate | 1.5924 |
| O,O—dimethyl O—(2-((1-methylethyl)thio)-5-pyrimidinyl) phosphate | 1.5068 |
| O,O—diethyl O—(2-((1,1-dimethyl)thio)-5-pyrimidinyl) phosphate | 1.5057 |
| O—ethyl S—(2-methylpropyl) O—(5-pyrimidinyl) phosphorodithioate | 1.5406 |
| O—ethyl S—(2-methylpropyl) O—(2-methyl-5-pyrimidinyl) phosphorodithioate | 1.5339 |
| O—ethyl S—(2-methylpropyl) O—(2-ethyl-5-pyrimidinyl) phosphorodithioate | 1.5296 |
| O—ethyl S—(2-methylpropyl) O—(2-(1-methylethyl)-5-pyrimidinyl) phosphorodithioate | 1.5269 |
| O—ethyl S—(2-methylpropyl) O—(2-(2-methylpropyl)-5-pyrimidinyl) phosphorodithioate | 1.5269 |
| O—ethyl S—(2-methylpropyl) O—(2-(methylthio)methyl-5-pyrimidinyl phosphorodithioate | 1.5589 |
| O—ethyl S—(2-methylpropyl) O—(2-(ethylthio)methyl-5-pyrimidinyl) phosphorodithioate | 1.5522 |
| O—ethyl S—(2-methylpropyl) O—(2-(ethyl-4-methyl-5-pyrimidinyl) phosphorodithioate | 1.5284 |
| O—ethyl S—(2-methylpropyl) O—(2-methylthio-5-pyrimidinyl) phosphorodithioate | 1.5696 |
| O—ethyl S—(2-methylpropyl) O—(2-(1-methylethyl)-thio-5-pyrimidinyl) phosphorodithioate | 1.5548 |
| O—ethyl S—(2-methylpropyl) O—(2-((methylthio)ethylthio)-5-pyrimidinyl) phosphorodithioate | 1.5881 |

The compounds of the present invention are useful as pesticides in agricultural operations in the control of chewing and sucking type insects which attack valuable crops.

The compounds which have an alkylthio or (alkylthio)ethylthio substituent in the two position of the pyrimidinyl ring and all of the compounds which are mixed esters, i.e., having an S-alkyl group on the phosphorus have relatively low mammalian toxicity and are suitable for foliar application to field crops and orchard trees in the control of beet armyworm, cabbage looper, tobacco budworm, cotton leafworm, pink bollworm, spiny bollworm, grape berry moth, leafhoppers and rice stem borer. These compounds are also effective against western spotted cucumber beetle larvae indicating good activity against corn rootworm. These compounds are particularly effective in the control of codling moth.

The present novel compounds having an alkyl or an alkylthioalkyl group are useful for controlling most insects but are especially suitable for soil application due to the excellent stability in soil. These compounds have outstanding activity against western spotted cucumber beetle and corn rootworm and are also useful in the control of insects such as thrips on corn, cotton and sorghum and leafhoppers on sugar beets by soil application.

Compositions comprising one or a mixture of the present pyrimidinyl phosphates or thiophosphates or dithiophosphates as an active ingredient in association with various agricultural or pesticidal carriers, surface-active agents and other additaments are very useful for the control of undesirable insect pests. It is an advantage of the present invention that compositions containing the present compounds can be applied to soil or to growing vegetation in amounts required for pest control without significant injury to plant foliage.

In carrying out the method of the present invention, the undesirable pests can be controlled by contacting the pest, its habitat, and/or its food prior to ingestion, with a pesticidal amount of the unmodified pyrimidinyl phosphate, thiophosphate or dithiophosphate. However, the present method also embraces the employment of a liquid, wettable powder, dust or granular composition containing the toxicant. Such compositions are adapted to be applied to living plants or to the locus thereof without substantial injury to the foliage or other parts thereof. In preparing toxicant compositions, the pyrimidinyl phosphate, thiophosphate or dithiophosphate product can be modified with one or more of a plurality of adjuvants including aromatic solvents, petroleum distillates, surface-active dispersing agents, wettable powder, or finely divided inert solids, the latter as a dust or granule. Depending upon the concentration in the composition of the active product, such augmented compositions are adapted to be applied to insect pests, their habitats or their foods, or employed as concentrates and subsequently diluted with additional inert carrier to produce the ultimate treating compositions. In compositions to be employed as concentrates, the toxicant can be present in a concentration of from about 5 to about 98% by weight.

The exact concentration of the pyrimidinyl phosphate, thiophosphate or dithiophosphate product employed in a composition for application to the pest, its habitat or food, can vary provided a pesticidal dosage of toxicant is supplied either on the pest or its environment or in its food. This dosage of toxicant is primarily dependent upon the susceptibility of a particular pest to the pyrimidinyl phosphate, thiophosphate or dithiophosphate compound. Good results are obtained with liquid compositions containing the active toxicant in the amount of, by weight, from 0.5 to 2000 parts or more per million, but preferably about 1 to about 400 ppm. Compositions containing as high as 90% by weight of toxicant are sometimes conveniently employed. With dusts and granules good results are obtained with compositions containing from about 0.05 to about 50% by weight, more preferably about 1 to about 20% by weight and most preferably about 2.5 to about 15% by weight of toxicant.

In the preparation of dust or granulated compositions, the pyrimidinyl phosphate, thiophosphate or dithiophosphate compound can be compounded with any of the finely divided solids such as pyrophyllite, diatomaceous earth, gypsum and the like. In such operations, the finely divided carrier is ground or mixed with the toxicant or wet with a solution of the toxicant in a volatile organic solvent. Similarly, dust compositions containing the pyrimidinyl phosphate or thiophosphate product can be compounded from various of the solid surface active dispersing agents, such as fullers earth, attapulgite, bentonite and other clays. Depending upon the proportions of ingredients, these dust compositions can be employed as concentrates and subsequently diluted with additional solid surface active dispersing agent or with pyrophyllite, diatomaceous earth, gypsum and the like to obtain the desired amount of active ingredient in a composition adapted to be employed for the control of pests. Also such concentrate dust compositions can be dispersed in water, with or without the aid of dispersing agents, and wetting agents, to form spray mixtures.

Further, the pyrimidinyl phosphate, thiophosphate or dithiophosphate compound or a dust concentrate composition containing such compound can be incorporated in intimate mixture with surface active dispersing agents such as ionic and non ionic emulsifying agents to form spray concentrates. Wherein such composition is a dust concentrate, it becomes a wettable powder when suitably formulated with emulsifying and/or wetting agents as understood in the art. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

While a composition of the toxicant in admixture with an inert or stabilized finely divided solid such as a montmorillonite clay may be granulated by well known methods to provide a granular product, it is preferred to provide a granulated solid carrier such as creekonite granules commercially prepared from a montmorillonite type clay, preferably containing a small amount of butyrolactone or stabilizer and to add the requisite around of toxicant by spraying on toxicants melted if necessary, or a solution of toxicant in a volatile solvent such as methylene chloride, as in a moving bed operation. The toxicant is imbibed by the granules. Any solvent present is removed in a drying operation. Preferred sized granules are about 24–48 mesh (U.S. Sieve Series).

The pyrimidinyl phosphate, thiophosphate or dithiophosphate compound can be compounded with a suitable water-immiscible organic liquid and surface active dispersing to produce emulsifiable liquid concentrates which can be further diluted with water to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil soluble and include the non-ionic emulsifiers such as the polyoxyethylene derivatives of sorbitan esters, complex ether alcohols and the like. However, oil-soluble ionic emulsifying agents such as mahogany soaps or alkylbenzene sulfonates such as dodecylbenzene sulfonate or alkyl napthaline sulfonates can also be used. Suitable organic liquids to be employed in the compositions include petroleum oils and distillates toluene, xylene, liquid halohydrocarbons, ketones and synthetic oils.

Similarly, invert emulsions can be made and employed if desired.

When operating in accordance with the present invention, the pyrimidinyl phosphate, thiophosphate or dithiophosphate compound or a composition containing the toxicant is applied to the pests to be controlled, to their habitat, including the soil or to their food, in any convenient fashion, for example by means of hand dusters or sprayers or by simple mixing with the food to be ingested by the pests. Applications to foliage of plants is conveniently carried out wiith power dusters, boom sprayers and spray dusters. In such foliar applications, the employed compositions should not contain any appreciable amounts of any chyto-toxic diluents or additaments. In large scale operations, dusts or low-volume sprays can be applied as from an airplane. Application to the soil is conveniently carried out with spray applicators including boom sprayers followed by working of the soil as with a disc harrow or other harrow. Soil application is also conveniently carried out at the time of planting by delivering composition in the form of a dust or granule into the seed furrow, or preferably by applying the granules in a band above the seed row usually with light soil incorporation.

For soil application, compositions containing the active toxicant are applied in an effective amount in the range of about 0.1 to about 5 pounds per acre, more preferably about 0.1 to about 2 pounds per acre. The most active toxicants amongst the present new compounds are effective at an application rate of about 1.0 pound per acre substantially without injury to growing crops.

The control of pests by the administration of the present novel pyrimidinyl phosphates, thiophosphates or dithiophosphates is illustrated by the following examples.

EXAMPLE 6

In separate operations, aqueous compositions of the present pyrimidinyl phosphate, thiophosphate or dithiophosphate toxicant compounds are prepared as follows:

Four parts by weight of each respective toxicant compound, 0.08 part of sorbitan trioleate (Span 85) and 0.02 part of a sorbitan monolaurate polyoxyethylene derivative (Tween 80) are dispersed in 40 milliliters of acetone to produce a concentrate composition in the form of a water dispersible liquid. This concentrate composition is dispersed in water to provide aqueous compositions containing varying amounts of the toxicant.

Also, the respective toxicant compounds are formulated in water with an alkyl aryl sulfonate (Nacconol NR) and a substituted benzoid alkyl sulfonic acid (Daxad No. 27) to produce aqueous compositions. In such operations, the materials are ballmilled together to produce compositions containing varying amounts of one of the toxicants, 300 parts by weight of Nacconol NR and 300 parts by weight of Daxad No. 27.

Aqueous compositions prepared according to the foregoing have very desirable wetting properties and are especially adapted to be applied to such undesirable pests as aphids, mites and insects, or to their habitats and food for the control of the pests.

EXAMPLE 7

An aqueous spray composition containing 25 parts per million of 0,0-diethyl 0-(2-methylthio-5-pyrimidinyl) phosphorothioate is prepared according to the procedures for the Span 85 type formulation set forth in Example 6. Also aqueous spray compositions containing 6.25 parts per million of the following compounds are similarly prepared.

O,O-diethyl O-(2-(1-methylethyl)-5-pirimidinyl) phosphorothioate; O,O-diethyl O-((2-methylthio)ethylthio-5-pyrimidinyl) phosphorothioate; O,O-dimethyl O-(2-(1;1-dimethylethyl)thio-5-pyrimidinyl) phosphorothioate; O-ethyl S-propyl O-(2-(1-methylethyl)-5-pyrimidinyl) phosphorodithioate; O,O-diethyl O-(2-(1-methylethyl)-4methyl-5-pyrimidinyl)phosphorothioate.

These compositions are poured over respective newtown pippin apples each having closely associated therewith 50–100 codling moth (*Laspeyresia pomonella*) eggs. In each case one of the test compositions is poured over the apple and the associated eggs. The treated apples are allowed to incubate in the greenhouse for about 12 days. Observations show that in each case there is complete control of the codling moth due to treatment with the test compound.

On testing the same compounds in an orchard setting wherein fruit is maturing on various species of apple trees infested with codling moth eggs, the same excellent control is obtained.

EXAMPLE 8

In additional operations test compositions are prepared according to the Span 85 procedure of Example 6 containing, in each case, 400 ppm of the toxicant. In each case 75 gram portions of air-dried soil is treated with sufficient test composition, about 5 ml, to provide 25 ppm of toxicant in the soil after 24 hours of air drying. Each portion of treated soil is stirred until well mixed and divided and added to 2 vials previously infested with 50–100 western spotted cucumber beetles (*Diabrotica undecimpunctata undecimpunctata*) eggs. A grain of corn is planted in each vial and the vials watered and incubated in a warm humid environment. After 12 days the corn plants are rated for damage and any larvae present noted. The absence of larvae in the vials indicates 100% control.

Complete control was observed in tests employing the following compounds: O,O-diethyl O-(2(1-methylethyl)-5-pyrimidinyl) phosphorothioate; O,O-diethyl O-(2 5-pyrimidinyl) phosphorothioate; O,O-diethyl O-(2-methylthio-5-pyrimidinyl) phosphorothioate; O,O-diethyl O-(2 me==hyl-sulfinyl-5-pyrimidinyl) phosphorothioate; O,O-dimethyl O-(2-(1,1-dimethylethyl)-5-pyrimidinyl) phosphorothioate; O-ethyl S-propyl O-(2-methyl-5-pyrimidinyl) phopshorothioate; O-ethyl S propyl O-(2-(1-methylethyl)-5-pyrimidinyl) phosphorodithioate; O,O-diethyl O-(2(1,1-dimethylethyl)thio-5-pyrimidinyl) phosphate; O-ethyl S-(2-methylpropyl) O-(2-methylthio-5-pyrimidinyl) phosphorodithioate and O,O-dimethyl O-(2-((1methylethl) O-(2-((1-methylethyl)sulfonyl)-5-pyrimidinyl) phosphorothioate.

EXAMPLE 9

On repeating the tests of Example 8 at toxicant composition concentrations in the air dried soil of 25, 6.25 and 1.5 ppm utilizing one of the present compounds O,O-diethyl O-(2-(1methylethyl)-5-pyrimidinyl) phosphorothioate and a comparison prior art compound O,O-diethyl O (2-(1-methylethyl)-4-methyl 6-pyrimidinyl) phosphorothioate and calculating the approximate $LC_{90}$ in ppm western spotted cucumber beetle larvae the present compound was computed to have an $LC_{90}$ of less than 1.5 ppm while that of the prior art compound was greater than 4 ppm.

EXAMPLE 10

Respective portions of creekonite (montmorillionite clay) granules containing a small amount of butyrolactone are impregnated with respective methylene chloride solutions of O,O-diethyl O-(2-(1-methylethyl)-5-pyrimidinyl) phosphorothioate (Compound A) and O,O-diethyl O-(2-(1,1-dimethylethyl)-5-pyrimidinyl) phosphorothioate (Compound B) and dried to remove the solvent to provide respective portions of granules containing about 10 percent by weight of the respective compounds.

The granular compositions are placed into the seed furrows and also in respective areas as a band at planting of regular hybrid field corn at the rate of 0.25 and 0.5 pound active toxicant per acre for each compound in respective field plots of good agricultural soil in the Midwestern U.S.A. Adjacent plots are left untreated as controls. From time to time the growing crops are inspected and an occasional plant is uprooted and the roots inspected. In plots treated with Compound A granules at 0.25 and 0.5 pound/acre and Compound B at 0.5 pound/acre greater than 90% control of thrips is achieved compared to the controls on inspection 14 days after germination. Examination of roots shows excellent control of northern and western corn rootworms at all dosages compared to the untreated controls. Further, at harvest time, each test plot shows a 20 to 25% greater yield of grain than the control plots.

EXAMPLE 11

On preparing granules containing Compounds A and B as in Example 10 and applying the granules to the furrow at the rate of 0.5 pound of toxicant per acre in planting sugar beet seedlings, greater than 90% leafhopper control is achieved for a period of at least 60 days.

EXAMPLE 12

On preparing granules containing Compounds A and B as in Example 10 and applying the same to the seed furrow on planting cotton seeds in good delta soil at the rates of 0.25, 0.5 and 1 pound of toxicant per acre for each compound, greater than 90% control of thrips is achieved for a period of at least 60 days from planting compared to untreated controls and substantially without phytotoxic effects on the foliage of the cotton plants from the germinated seeds.

Substantially each of the present compounds has been found active against each of the types of insects listed hereinabove when applied at a foliar application of 2000 ppm and more generally 400 ppm or less, e.g., 0.5 to 1.5 ppm or, where appropriate, in soil applications at 5 pounds per acre and more generally at 2 pounds per acre or less, e.g., 0.25 to 0.5 pound per acre.

The compounds act both systemically and as contact poisons to insects. Those compounds with a sulfur atom in the ring substituent, including the sulfinyl and sulfonyl group, exhibit somewhat more systemicity than those without a sulfur containing substituent. Those O,O-diethyl phosphorothioate compounds having alkyl in the 2-ring position constitute a preferred group to employ in the control of western spotted cucumber beetle and corn rootworm having good soil stability and adequate residuality and bringing about good grain crop increase in treated corn. These compounds are of advantage in that they do not readily leach from the soil.

The pyrimidinols employed as intermediates in the preparation of the present compounds are prepared according to methods described in the literature. 4,6-dimethyl-5-pyrimidinol and 2,4,6-trimethyl-5-pyrimidinol are prepared according to the method of A. Dornow and H. Hell, Chem. Ber. 93, 1998–2001 (1960), in which 3-chloro-2,4-pentanedione are reacted with formamide or acetamide to give the corresponding oxazole which is heated with ammona under pressure to give the desired 5-pyrimidinol.

The 2-alkyl-4-methyl-5-pyrimidinols are made by reacting methyl methoxyacetate with sodium hydride in toluene and directly reacted with the requisite amidine to give 2-alkyl-5-methoxy-6-methoxymethyl-4-pyrimidinol. This latter compound is chlorinated in the 4-position by reaction with phosphorus oxychlorides. The ring chlorine and the methoxy group in the methylmethoxy group are replaced with hydrogen on reduction with zinc in 1 normal NaOH and reaction with sodium ethyl mercaptan in dimethylformamide then yields the desired pyrimidinol.

In a preferred method of preparation of 2-alkyl-5-pyrimidinols or 2-alkylthio-5-pyrimidinols phosgene is bubbled into dimethylformamide in methylene chloride medium forming a Vilsmeier reagent which is then allowed to react with methoxyacetaldehyde. The appropriate amidine is then added to the reaction mixture followed by sodium methoxide in methanol. The methylene chloride is distilled or flashed off and the mixture heated under reflux to form the desired 2-alkyl-5-methoxypyrimidine. The methoxy group is converted to the OH group using sodium ethyl mercaptan in dimethylformamide.

I claim:

1. A compound of the formula

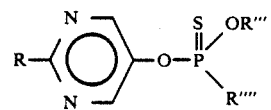

wherein
R is 1,1-dimethylethyl;
R''' is ethyl; and
R'''' is ethoxy.

2. A composition comprising an agricultural carrier selected from the group consisting of surface active dispersing agents and finely divided inert solids in admixture with a pyrimidinyl phosphate having the formula:

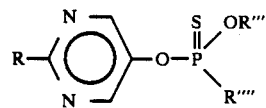

wherein
R is 1,1-dimethylethyl;
R''' is ethyl; and
R'''' is ethoxy.

3. A method which comprises applying to crop land soil an insecticidal amount but less than a phytotoxic amount of a pyrimidinyl phosphate having the formula

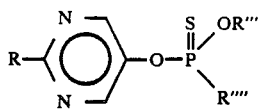

wherein
R is 1,1-dimethylethyl;
R''' is ethyl; and

R''' is ethoxy.

4. The method as in claim 3 in which the defined pyrimidinyl phosphate is applied to the soil of crop lands in an insecticidal amount.

5. The method as in claim 4 in which the defined pyrimidinyl phosphate is applied to the soil of corn, sorghum, cotton or sugar beets.

6. The method of claim 5 in which the defined pyrimidinyl phosphate is applied to the soil of corn at a rate in the range of about 0.1 to 2 pounds per acre.